US008562520B2

(12) United States Patent
Rockrohr

(10) Patent No.: US 8,562,520 B2
(45) Date of Patent: Oct. 22, 2013

(54) ACCESS PORT

(75) Inventor: Brian Rockrohr, Waterbury, CT (US)

(73) Assignee: Covidien LP, Mansfield, MA (US)

( * ) Notice: Subject to any disclaimer, the term of this patent is extended or adjusted under 35 U.S.C. 154(b) by 39 days.

(21) Appl. No.: 13/212,237

(22) Filed: Aug. 18, 2011

(65) Prior Publication Data
US 2012/0083661 A1   Apr. 5, 2012

Related U.S. Application Data

(60) Provisional application No. 61/388,627, filed on Oct. 1, 2010.

(51) Int. Cl.
*A61B 1/32* (2006.01)
*A61B 17/00* (2006.01)

(52) U.S. Cl.
USPC ..................................... 600/208; 604/167.03

(58) Field of Classification Search
CPC .................................. A61B 1/32; A61B 17/00
USPC ........ 600/202, 205–210; 604/167.01, 167.03, 604/167.06, 167.07, 264
See application file for complete search history.

(56) References Cited

U.S. PATENT DOCUMENTS

| | | |
|---|---|---|
| 4,177,814 A | 12/1979 | Knepshield et al. |
| 4,436,519 A | 3/1984 | O'Neill |
| 4,535,819 A | 8/1985 | Atkinson et al. |
| 5,010,925 A | 4/1991 | Atkinson et al. |
| 5,141,498 A | 8/1992 | Christian |
| 5,180,373 A | 1/1993 | Green et al. |
| 5,263,944 A | 11/1993 | Vidal et al. |
| 5,269,763 A | 12/1993 | Boehmer et al. |
| 5,282,790 A | 2/1994 | Clement |
| 5,300,033 A | 4/1994 | Miller |
| 5,300,035 A | 4/1994 | Clement |
| 5,312,362 A | 5/1994 | Pfolsgraf et al. |
| 5,324,270 A | 6/1994 | Kayan et al. |
| 5,330,437 A | 7/1994 | Durman |
| 5,354,280 A | 10/1994 | Haber et al. |
| 5,356,394 A | 10/1994 | Farley et al. |
| 5,380,288 A | 1/1995 | Hart et al. |
| 5,385,552 A | 1/1995 | Haber et al. |
| 5,391,153 A | 2/1995 | Haber et al. |

(Continued)

FOREIGN PATENT DOCUMENTS

| | | |
|---|---|---|
| EP | 1 520 537 A1 | 4/2005 |
| EP | 1 707 133 A1 | 10/2006 |

(Continued)

OTHER PUBLICATIONS

European Search Report EP 11 25 0773 dated Aug. 2, 2013.

*Primary Examiner* — Pedro Philogene

(57) ABSTRACT

A surgical access port assembly is provided including a cannula and an obturator insertable through the cannula. The cannula includes a housing having a hollow elongate tubular member extending distally from the housing. A duckbill valve is provided within the housing and includes an outer support rim and a pair of opposed multi-angle leaflets extending inwardly from the outer support rim. Each leaflet includes a lead in portion oriented at a first angle relative to the support rim and an entry portion extending from the lead in portion and oriented at a second angle relative to the support rim. The second angle is greater than the first angle.

18 Claims, 9 Drawing Sheets

(56) References Cited

U.S. PATENT DOCUMENTS

| | | |
|---|---|---|
| 5,401,248 A | 3/1995 | Bencini |
| 5,417,705 A | 5/1995 | Haber et al. |
| 5,431,667 A | 7/1995 | Thompson et al. |
| 5,441,486 A | 8/1995 | Yoon |
| 5,443,452 A | 8/1995 | Hart et al. |
| 5,492,304 A | 2/1996 | Smith et al. |
| 5,496,280 A | 3/1996 | Vandenbroek |
| 5,584,850 A | 12/1996 | Hart et al. |
| 5,603,702 A | 2/1997 | Smith et al. |
| 5,613,954 A | 3/1997 | Nelson et al. |
| 5,640,977 A | 6/1997 | Leahy et al. |
| 5,643,301 A | 7/1997 | Mollenauer |
| 5,657,963 A | 8/1997 | Hinchliffe et al. |
| 5,709,664 A | 1/1998 | Vandenbroek et al. |
| 5,788,676 A | 8/1998 | Yoon |
| 5,803,919 A | 9/1998 | Hart et al. |
| 5,813,409 A | 9/1998 | Leahy et al. |
| 5,820,600 A | 10/1998 | Carlson et al. |
| 5,820,604 A | 10/1998 | Fox et al. |
| 5,820,606 A | 10/1998 | Davis et al. |
| 5,857,999 A | 1/1999 | Quick et al. |
| 5,872,812 A | 2/1999 | Saito et al. |
| 5,906,595 A | 5/1999 | Powell et al. |
| 5,913,847 A | 6/1999 | Yoon |
| 5,989,232 A | 11/1999 | Yoon |
| 5,989,233 A | 11/1999 | Yoon |
| 6,066,117 A | 5/2000 | Fox et al. |
| D426,635 S | 6/2000 | Haberland et al. |
| 6,083,203 A | 7/2000 | Yoon |
| 6,086,603 A | 7/2000 | Termin et al. |
| 6,123,689 A * | 9/2000 | To et al. .......... 604/256 |
| D449,887 S | 10/2001 | Haberland et al. |
| 6,551,282 B1 | 4/2003 | Exline |
| 6,595,946 B1 | 7/2003 | Pasqualucci |
| 6,702,255 B2 * | 3/2004 | Dehdashtian .......... 251/149.3 |
| 7,001,404 B1 | 2/2006 | Chin |
| 7,011,314 B2 | 3/2006 | McFarlane |
| 7,112,185 B2 | 9/2006 | Hart et al. |
| 7,153,319 B1 | 12/2006 | Haberland et al. |
| 7,163,525 B2 * | 1/2007 | Franer ........... 604/167.03 |
| 7,169,130 B2 | 1/2007 | Exline et al. |
| D537,941 S | 3/2007 | Haberland |
| 7,300,399 B2 | 11/2007 | Bonadio et al. |
| 7,393,322 B2 | 7/2008 | Wenchell |
| 7,789,861 B2 | 9/2010 | Franer |
| 8,034,032 B2 * | 10/2011 | Voegele et al. .......... 604/167.03 |
| 8,092,431 B2 * | 1/2012 | Lunn et al. .......... 604/167.04 |
| 8,100,929 B2 * | 1/2012 | Franer et al. .......... 606/185 |
| 2002/0010424 A1 | 1/2002 | Dennis |
| 2002/0107484 A1 | 8/2002 | Dennis |
| 2002/0128602 A1 | 9/2002 | Adams et al. |
| 2004/0015185 A1 | 1/2004 | Ewers et al. |
| 2004/0171990 A1 | 9/2004 | Dennis |
| 2004/0204682 A1 | 10/2004 | Smith |
| 2005/0033342 A1 | 2/2005 | Hart et al. |
| 2005/0043682 A1 | 2/2005 | Kucklick et al. |
| 2005/0077688 A1 | 4/2005 | Voegele et al. |
| 2005/0131349 A1 | 6/2005 | Albrecht et al. |
| 2005/0212221 A1 | 9/2005 | Smith et al. |
| 2005/0216028 A1 | 9/2005 | Hart et al. |
| 2005/0222582 A1 | 10/2005 | Wenchell |
| 2006/0047284 A1 | 3/2006 | Gresham |
| 2006/0229565 A1 | 10/2006 | Dennis et al. |
| 2006/0247673 A1 | 11/2006 | Voegele et al. |
| 2006/0264991 A1 | 11/2006 | Johnson et al. |
| 2007/0004968 A1 | 1/2007 | Bonadio et al. |
| 2007/0088277 A1 | 4/2007 | McGinley et al. |
| 2007/0244426 A1 | 10/2007 | Hart et al. |
| 2010/0081863 A1 * | 4/2010 | Hess et al. .......... 600/37 |
| 2012/0089094 A1 * | 4/2012 | Franer et al. .......... 604/167.01 |

FOREIGN PATENT DOCUMENTS

| | | |
|---|---|---|
| EP | 1 709 918 A1 | 10/2006 |
| EP | 2 042 114 A1 | 4/2009 |
| EP | 2 087 846 A2 | 8/2009 |
| EP | 2172156 A1 | 4/2010 |
| WO | WO2004/096295 A2 | 11/2004 |
| WO | WO2005/102186 A1 | 11/2005 |
| WO | WO 2008/045744 A2 | 4/2008 |
| WO | WO 2008/093313 A1 | 8/2008 |

\* cited by examiner

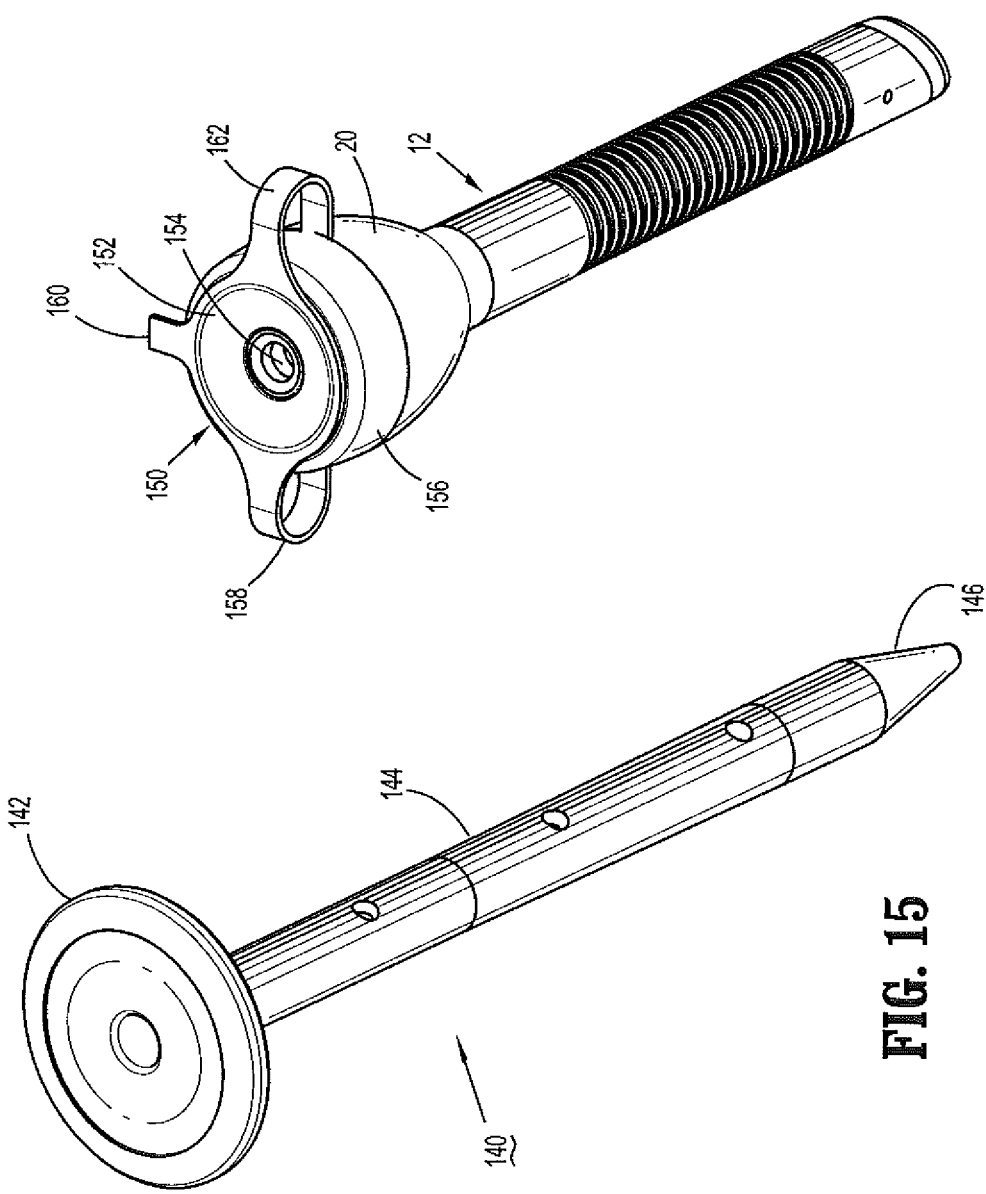

ACCESS PORT

CROSS-REFERENCE TO RELATED APPLICATION

The present application claims the benefit of, and priority to, U.S. Provisional Patent Application Ser. No. 61/388,627, filed Oct. 1, 2010, the entire contents of which is herein incorporated by reference in its entirety.

BACKGROUND

1. Technical Field

The present disclosure relates to a surgical cannula or access port. More particularly, the present disclosure relates to a surgical cannula having a multiangle duckbill seal.

2. Background of Related Art

During certain surgical procedures it is often necessary to inflate a body cavity in order to create a working space. In order to insert surgical instruments into the working space, access ports are needed to seal about the surgical instruments and prevent escape of the inflation fluids. Cannulas are surgical access ports used in conjunction with surgical instruments to perform surgical operations within the body of a patient. A cannula typically includes a housing having an elongate tubular member extending from the housing and one or more valves or seals positioned within the housing for sealing about the surgical instruments.

An instrument seal is provided within the housing and includes a small opening for sealing about the surgical instrument. In order to prevent the escape of inflation fluids through the small opening of the instrument seal in the cannula in the absence of a surgical instrument, there is provided a duckbill valve seal having a pair of opposed, inwardly angled plates or flaps which meet at opposed edges. Inflation pressure traveling back up through the elongate tubular member of the cannula forces the opposed flaps together to prevent escape of the inflation fluids through the housing.

During many surgical procedures it is often necessary to repeatedly insert the same or different instruments through the cannula. In some instances, this can cause wear and tear problems with the duckbill seal due to the angle of the flaps and the materials used to form the duckbill seal.

Therefore, it is desirable to provide a cannula having a duckbill seal including flaps oriented to reduce wear problems due to repeated insertion of surgical instruments. It is additionally desirable to provide a cannula having a duckbill seal formed of a material chosen to reduce wear problems.

SUMMARY

There is disclosed a surgical access port including a hollow housing having a hollow elongate tubular member extending from the housing and a duck bill valve postioned within the housing. The duckbill valve has an outer support rim and first and second opposed flaps or leaflets extending inwardly of the outer support rim. Each leaflet includes a lead in portion oriented at a first angle relative to the outer support rim and an entry portion extending from the lead in portion and oriented at a second angle relative to the outer support rim. The first and second angles are different and the second angle is greater than the first angle.

The surgical access port further includes a reinforcing rib on each of the first and second leaflets. The reinforcing ribs traverse both the lead in portions and entry portions of the first and second leaflets and are centrally located on the first and second leaflets.

The surgical access port additionally includes an instrument seal positioned within the housing proximal to the duckbill valve and an end piece on a proximal end of the housing and having an opening for receipt of surgical instruments.

In one embodiment, the duckbill valve is formed of a synthetic rubber material. In a more specific embodiment, the duckbill valve is formed of a polyisoprene having a durometer of shore 30-40.

The surgical access port may further include a removable reducer cap positioned on the housing for sealing about small diameter surgical instruments.

In one embodiment, the elongate tubular member includes an enlarged indicia ring to limit the depth of penetration of the elongate tubular member relative to the body of the patient.

There is also disclosed a surgical access port assembly having a cannula including a hollow housing having a hollow elongate tubular member extending from the housing and a duckbill valve portioned within the housing. The duckbill valve has an outer support rim and first and second opposed leaflets extending inwardly of the outer support rim. Each leaflet includes a lead in portion oriented at a first angle relative to the outer support rim and an entry portion extending from the lead in portion and oriented at a second angle relative to the outer support rim. The surgical access port assembly further includes an obturator insertable through the cannula and having an elongate member terminating in a smooth obturator tip.

In one embodiment, the smooth obturator tip has a rounded distal tip. In an alternative embodiment, the smooth obturator tip has a conical distal tip.

There is further disclosed a surgical access port including a hollow housing and a hollow elongate tubular member extending from the housing. The elongate tubular member includes a rigid proximal portion, a flexible central portion and a rigid distal portion. A duckbill valve is postioned within the housing and has an outer support rim and first and second opposed leaflets extending inwardly of the outer support rim. Each leaflet includes a lead in portion oriented at a first angle relative to the outer support rim and an entry portion extending from the lead in portion and oriented at a second angle relative to the outer support rim.

The flexible portion is corrugated and includes a plurality of ribs. The flexible portion is bendable so as to orient the rigid distal portion up to 180° relative to the rigid proximal portion. In a specific embodiment, the flexible portion is longitudinally extendable.

DESCRIPTION OF THE DRAWINGS

Embodiments of the presently disclosed surgical access ports or cannula assemblies are disclosed herein with reference to the drawings, wherein:

FIG. 15 is a perspective view of an alternative embodiment of an obturator; and

FIG. 16 is a perspective view of the cannula with a reducer cap installed on a housing of the cannula.

DETAILED DESCRIPTION OF EMBODIMENTS

Embodiments of the presently disclosed surgical access ports or cannula assemblies will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
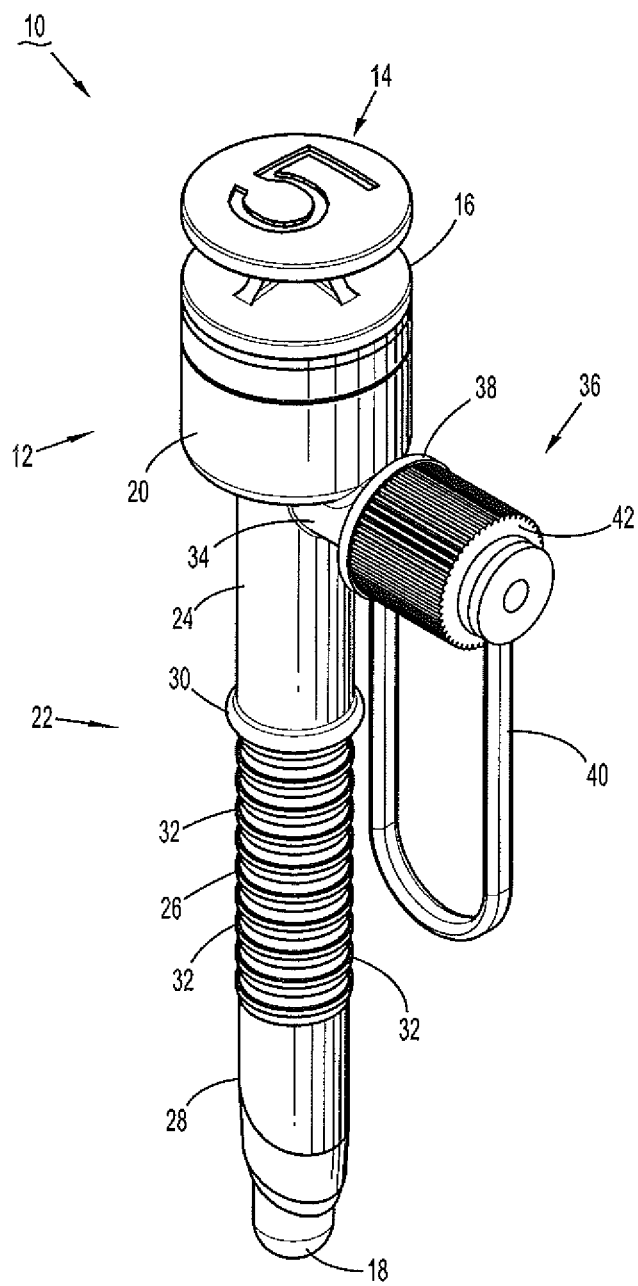
FIG. 1 is a perspective view of one embodiment of a cannula and obturator.
Figure 2:
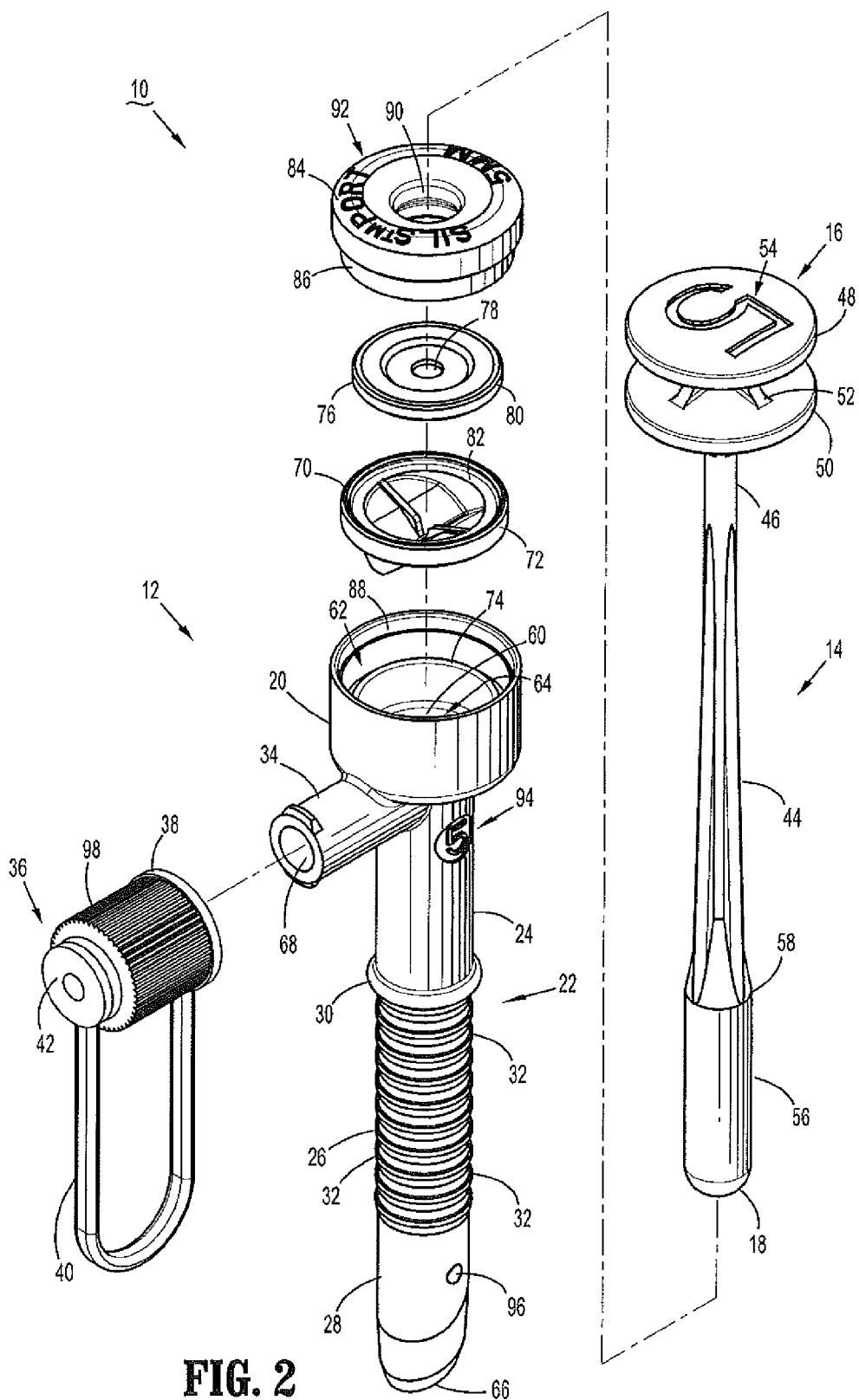
FIG. 2 is a perspective view, with parts separated, of the cannula and obturator.

Referring to FIGS. 1 and 2, there is disclosed a surgical access port or cannula assembly 10 including a cannula 12 and an obturator 14. Obturator 14 extends through cannula 12 and includes an end cap 16 and a rounded distal tip 18. Cannula 12 generally includes a housing 20 and an elongate tubular member 22 extending distally from housing 20. Elongate tubular member 22 is provided to be inserted through an auxiliary access port and has a smooth, a rigid proximal portion 24 extending distally from housing 20 and a central ribbed or corrugated portion 26 extending distally from proximal portion 24. A smooth, rigid distal terminal portion 28 extends distally from corrugated portion 26. An enlarged indicia ring 30 is formed between proximal portion 24 and corrugated portion 26 and assists a user in determining the proper depth of insertion of cannula 12 through an auxiliary access port in a manner described in more detail hereinbelow.

Corrugated portion 26 is formed with a plurality of ribs 32 which render corrugated portion flexible and/or elongatable relative to proximal portion 24 and distal portion 28.

An insufflation or valve port 34 is provided on housing 20 for providing insufflation fluid into the body of a patient. A tethered cap assembly 36 is provided to cover valve port 34 and includes a base 38 secured to valve port 34. A flexible tether 40 connects a removable cap 42 to base 38. Cap 42 is removably attached to valve port 34.

Referring now to FIG. 2, obturator 14 includes an elongate fluted member 44. An end cap 16 is provided at a proximal end 46 of elongate fluted member 44. End cap 16 includes an upper cap plate 48 and a lower cap plate 50 connected by a connector 52. Plates 48 and 50 facilitate grasping of obturator 14 by a user. Indicia 54 are provided on upper plate 48 to label the size of obturator 14. A smooth obturator tip 56 is provided at a distal end 58 of elongate fluted member 44 and terminates in rounded distal tip 18. Distal tip 18 is rounded to facilitate insertion of obturator 14 and cannula 12 through an incision in the patient or through an auxiliary access port.

As noted above, cannula 12 is provided to facilitate the insertion of surgical instruments into the body of the patient. Elongate tubular member 22 includes an open proximal end 60 which is open to an interior 62 of housing 20. Elongate tubular member 22 includes a through bore 64 which extends from open proximal end 60 to an open distal end 66 of elongate tubular member 22. A port bore 68 extends through insufflation valve port 34 and is in fluid communication with interior 62 of housing 20.

In order to prevent the escape of insufflation fluids through interior 62 of housing 20 in the absence of a surgical instrument, a duckbill valve 70 is provided within housing 20. Specifically, an outer support rim 72 of duckbill valve 70 is seated against an inner lip 74 of housing 20. In order to prevent the escape of insufflation fluids when a surgical instrument is inserted through duckbill valve 70, an instrument seal 76 is provided within interior 62 of housing 20. Instrument seal 76 includes a central opening 78 which is configured to seal about the body of a surgical instrument inserted there through. An outer rim 80 of instrument seal 76 is seated against an inner edge 82 of instrument seal 70.

An end piece 84 is provided to retain duckbill valve 70 and instrument seal 76 within housing 20. End piece 84 includes a reduced rim 86 which seats within an inner edge 88 of housing 20. End piece 84 includes a bore 90 for receipt of surgical instruments and additionally includes indicia 92 indicating the size of the surgical instruments to be utilized with cannula 12. As shown, indicia 94 may additionally be provided on elongate tubular member 22 to also indicate the size of the surgical instruments to be utilized with cannula 12. A vent hole 96 is provided on terminal portion 28 of elongate tubular member 22 to assist in venting insufflation gases into the body cavity of the patient. Removable cap 42 of tethered cap assembly 36 includes a ribbed outer surface 98 to facilitate grasping of cap 42 by a user.

Figure 3:
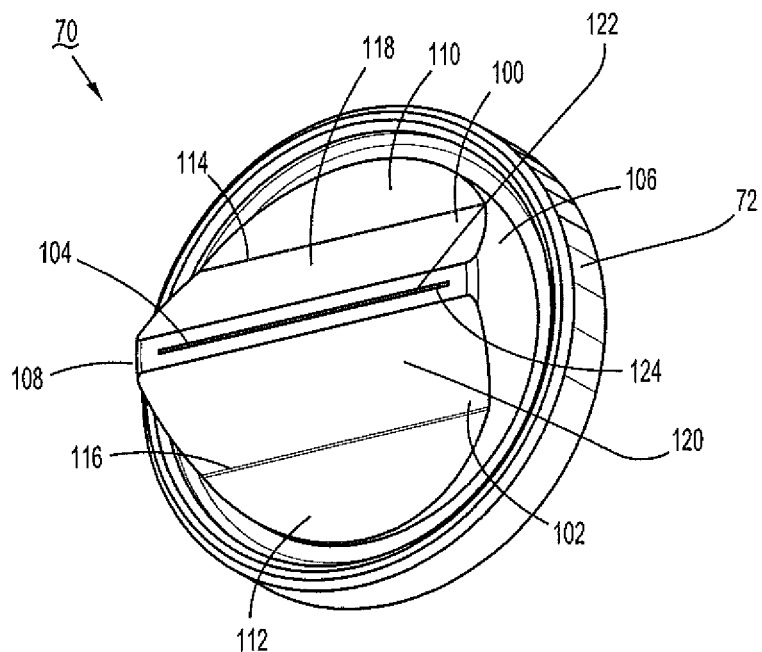
FIG. 3 is a perspective view, taken from below, of a duckbill seal of the cannula.

Referring now to FIGS. 3-10 the structure of duckbill valve 70 will now be described. Referring initially to FIG. 3, duck bill valve 70 is formed from a flexible material and includes a first multi-angle leaflet 100 and a second multi-angle leaflet 102. First and second leaflets 100 and 102 define a slit 104 there between for receipt of surgical instruments. Sides 106 and 108 extend from outer rim 72 to complete the seal about first and second leaflets 100 and 102. In order to reduce the strain and wear on first and second leaflets 100 and 102 due to repeated insertion of surgical instruments there through, first and second leaflets 100 and 102 include respective first and second lead in leaflets 110 and 112. First and second lead in leaflets 110 and 112 terminate in respective transition edges 114 and 116. First and second entry leaflets 118 and 120 extend radially inwardly from transition edges 114 and 116 respectively. First and second entry leaflets 118 and 120 terminate in respective seal lips 122 and 124 which define slit 104 therebetween.

Figure 4:
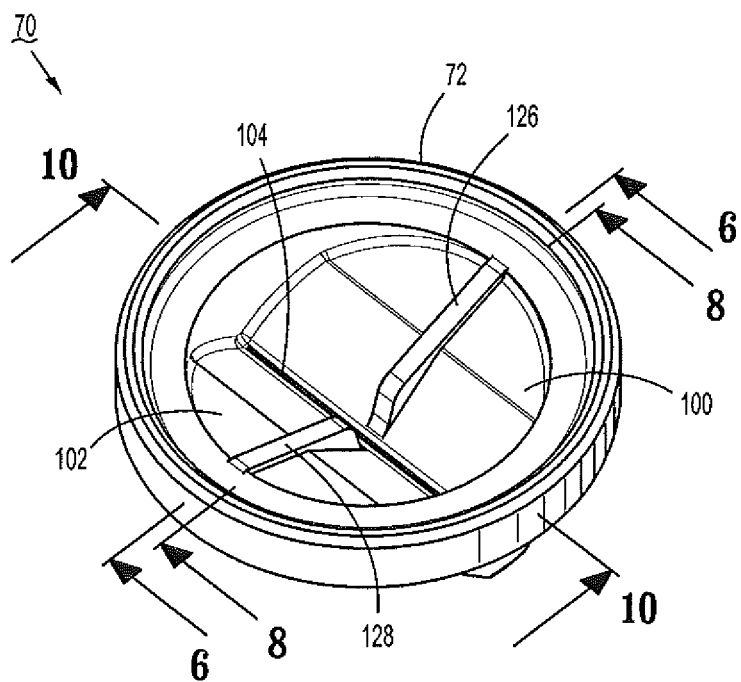
FIG. 4 is a perspective view, taken from above, of the duckbill seal.

Referring for the moment to FIG. 4, first and second leaflets 100 and 102 are provided with respective reinforcing ribs 126 and 128 which traversed first and second leaflets 100 and 102 and extend from outer rim 72 to slit 104. Reinforcing ribs 126 and 128 are centrally located on first and second leaflets 100 and 102. Reinforcing ribs 126 and 128 further assist in reducing the strain and where on first and second leaflets 100 and 102 as well as assist in maintaining the shapes of first and second leaflets 100 and 102 during repeated insertions of surgical instrumentation.

Figure 5:
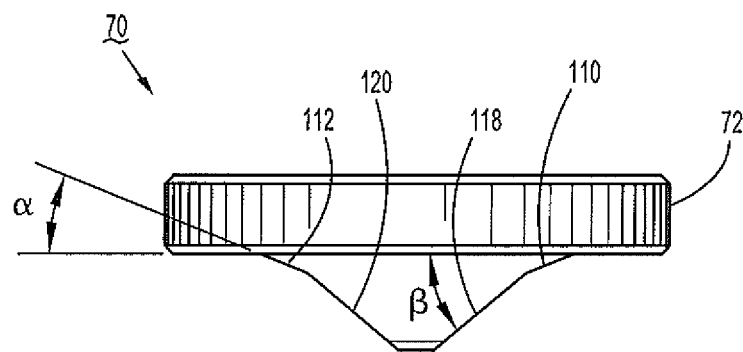
FIG. 5 is a side elevation view of the duckbill seal.
Figure 6:
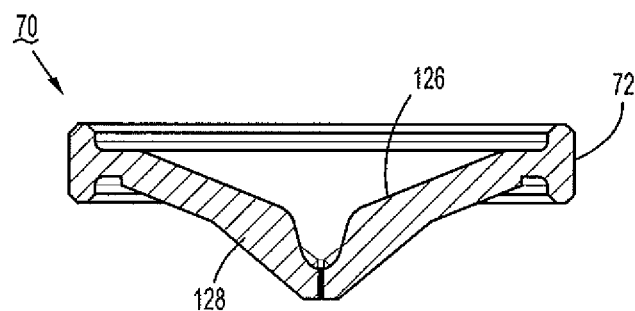
FIG. 6 is a cross sectional view taken along line 6-6 of FIG. 4.
Figure 7:
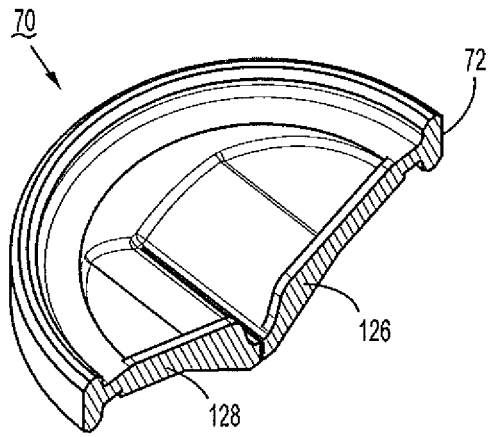
FIG. 7 is a perspective view, taken from above, and partially shown in section.
Figure 8:
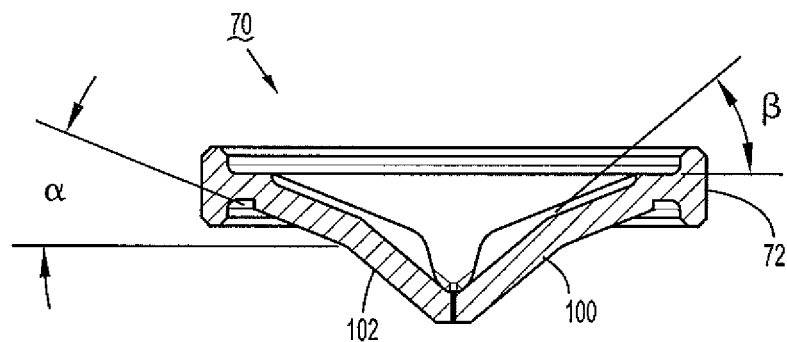
FIG. 8 is a cross sectional view taken along line 8-8 of FIG. 4.

Referring now to FIGS. 5 and 8, it can be seen that first and second lead in leaflets 110 and 112 are formed at different angles than first and second entry leaflets 118 and 120 relative to outer support rim 72. Specifically, first and second lead in leaflets 110 and 112 are formed at a relatively shallow angle $\alpha$ relative to outer support rim 72 while first and second entry leaflets are formed at a steeper angle $\beta$ relative to outer support rim 72.

Figure 9:
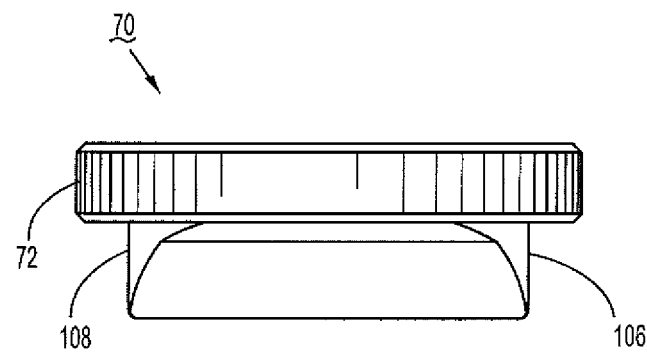
FIG. 9 is an end elevation view of the duckbill seal.
Figure 10:
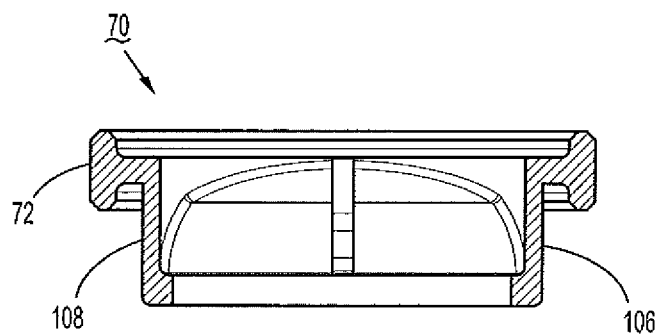
FIG. 10 is a cross sectional view taken along line 10-10 of FIG. 4.

As best shown in FIGS. 6-10, duckbill valve 70 is formed as a unitary, flexible structure. Duckbill valve 70 is formed from a synthetic rubber, such as polyisoprene, having a relative durometer of between Shore 30-40. First and second leaflets 100 and 102 are formed integral with outer rim 72 (FIG. 8). Likewise, central reinforcing ribs 126 and 128 are formed integral with outer rim 72 (FIGS. 6 and 7) and first and second leaflets 100 and 102 (FIG. 8). As best shown in FIGS. 9 and 10, sides 106 and 108 are also formed integral with outer rim 72. While not specifically shown, sides 106 and 108 are also integrally formed with first and second leaflets 100 and 102 to form a unitary structure.

Figure 11:
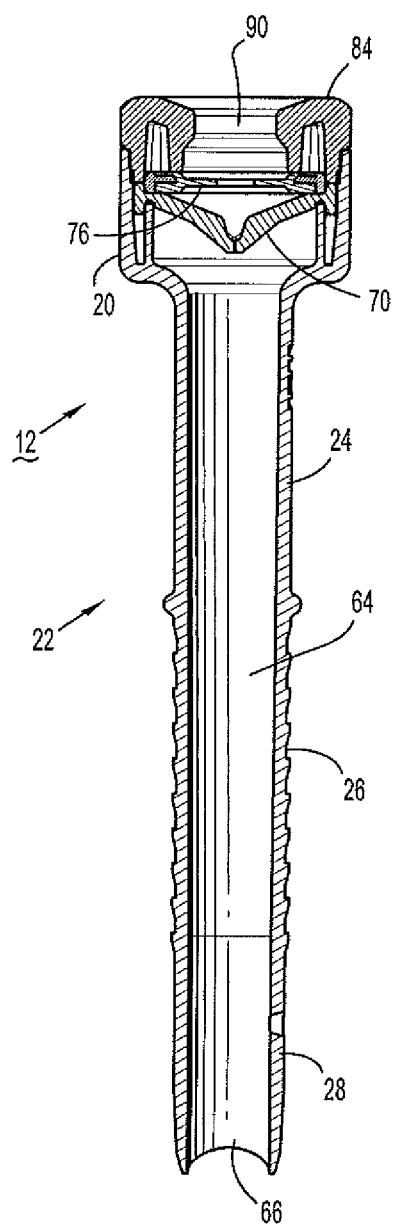
FIG. 11 is a cross sectional view of the cannula.

Referring now to FIG. 11, as noted here and above, elongate tubular member 22 is hollow and defines through bore 64 which has an open distal end 66. End piece 84 includes a bore 90 which is in fluid communication with interior 62 (FIG. 2) of housing 20. Interior 62 of housing 20 is in fluid communication with bore 64 of elongate tubular member 22.

Figure 12:
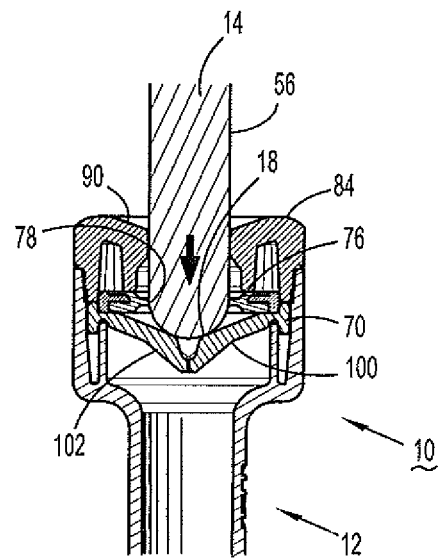
FIG. 12 is a partial cross sectional view of the cannula during initial insertion of the obturator.
Figures 13, 13A:
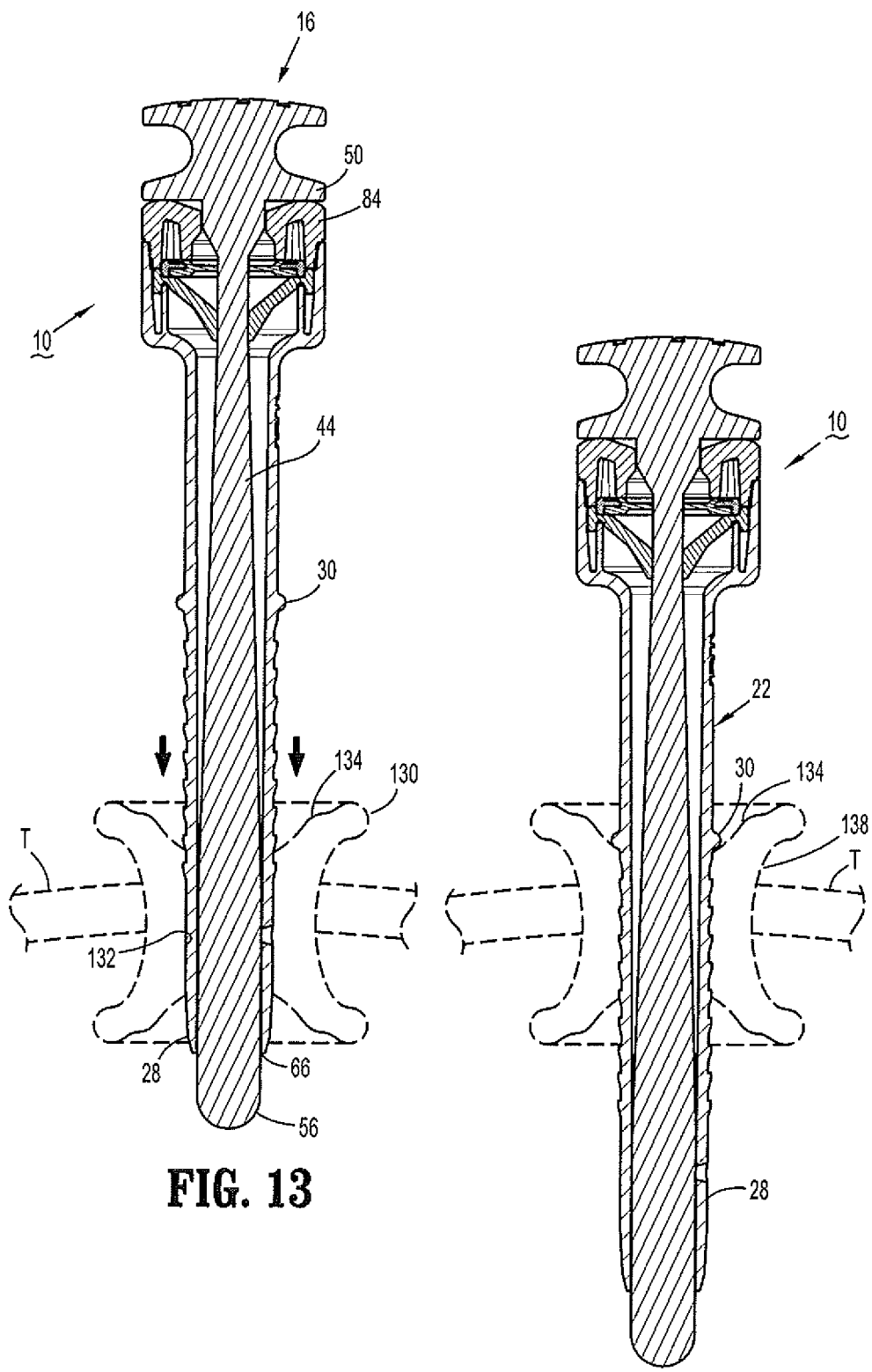
FIG. 13 is a cross sectional view of the cannula with the obturator fully inserted through the cannula.
FIG. 13A is a cross sectional view of the cannula with the obturator fully inserted through the cannula and a distal portion of the obturator extending distally below the cannula.

With reference to FIGS. 12 and 13, in order to assemble cannula assembly 10, smooth obturator tip 56 of obturator 14 is initially inserted through bore 90 of end piece 84 such that rounded distal tip 18 engages first and second leaflets 100 and 102 of duckbill valve 70. Obturator 14 continues to be advanced through cannula 12 until smooth obturator tip 56 exits open distal end 66 of elongate tubular member 22 (FIG. 13).

Cannula assembly 10 is of a very small diameter, on the order of approximately 5 mm, and thus during a surgical procedure it is often necessary to provide an auxiliary port, such as, for example, auxiliary single incision port 130 through a tissue section T to stabilize cannula assembly 10. Thus, as shown in FIG. 13, cannula assembly 10 is advanced through a passageway 132 of port 130 until enlarged indicia ring 30 engages a proximal end 134 of port 130 (FIG. 13A). As noted herein above, enlarged indicia ring 30 is provided to ensure that distal terminal portion 28 of elongate member 22 is inserted to the proper depth within a body cavity without risk of damaging underlying tissue.

Figure 14:
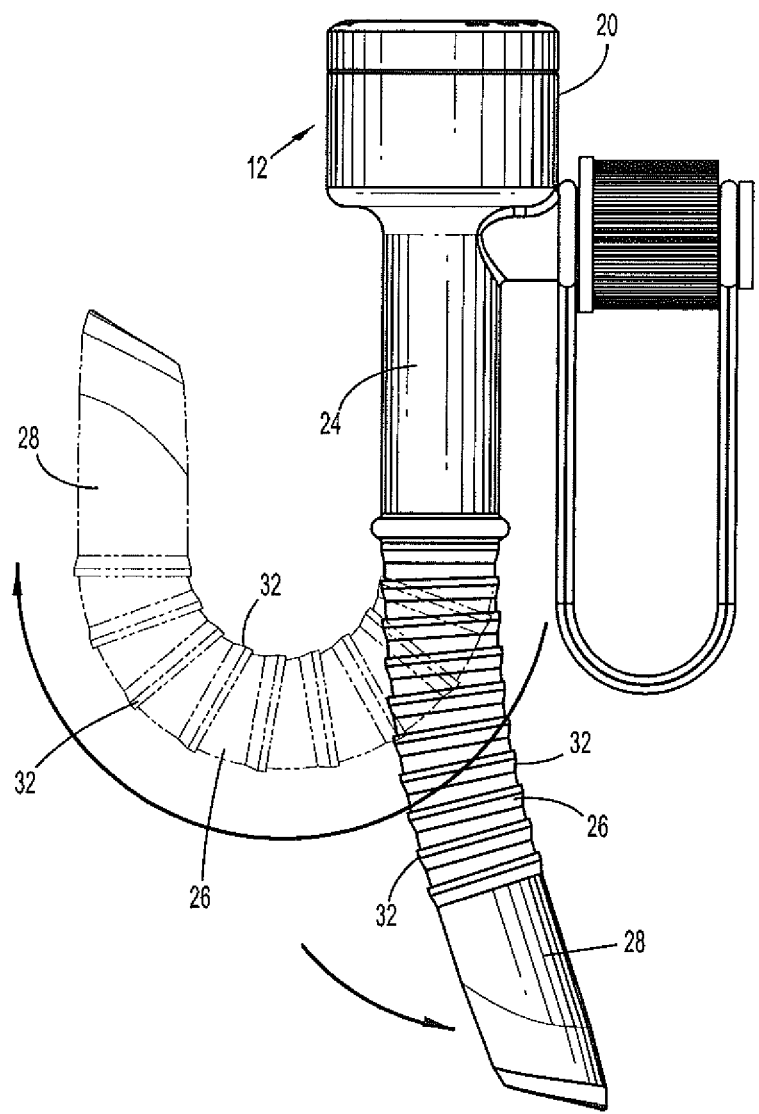
FIG. 14 is a side view of the cannula during flexation.

Referring for the moment to FIG. 14, as noted herein above, central corrugated or ribbed portion 26 of elongate tubular member 22 is flexible and can be bent in a variety of directions relative to housing 20 to facilitate accommodating various surgical instruments or to follow the bending of steerable surgical instruments. As shown, central corrugated portion 26 may be bent so as to reorient distal terminal portion 28 up to 180° with respect to smooth proximal portion 24. While not specifically shown, and as further noted herein above, central corrugated portion 26 may also be expandable in length by stretching ribs 32 of central corrugated portion 26 in an accordion fashion.

With reference to FIG. 15, there is disclosed an alternate embodiment of an obturator 140. Obturator 140 includes a proximal end cap 142 and an elongate tubular member 144 extending distally from proximal end cap 142. Elongate tubular member 144 terminates in a conical distal tip 146.

Referring now to FIG. 16, there is disclosed a reducer cap 150 for use with cannula 12. Reducer cap 150 is provided to seal about surgical instruments having a diameter too small to properly seal within opening 78 of instrument seal 76 (FIG. 2). Reducer cap 150 includes a concave entrance piece 152 defining an opening 154 for sealing about surgical instruments inserted therethrough. An attachment collar 156 is provided and is removably mounted on housing 20 of cannula 12. Flexible bands 158, 160 and 162 connect concave entrance piece 152 to attachment collar 156 and allow concave entrance piece 152 to be moved between a position overlying housing 20 to a position remote from housing 20.

It will be understood that various modifications may be made to the embodiments disclosed herein. For example, the angles of the lead in and entry portions of the first leaflet may be different from the angles of the lead in and entry portions of the second leaflet. Further, the disclosed multiangle leaflets may have more than two distinct portions. Additionally, the reinforcing ribs of the leaflets may be offset relative to each other. Still further, each leaflet may have more than one reinforcing rib. Therefore, the above description should not be construed as limiting, but merely as exemplifications of particular embodiments. Those skilled in the art will envision other modifications within the scope and spirit of the claims appended hereto.

The invention claimed is:

1. A surgical access port comprising:
   a hollow housing having a hollow elongate tubular member extending from the housing;
   a duckbill valve positioned within the housing and having an outer support rim and first and second opposed leaflets extending inwardly of the outer support rim, each leaflet including a lead in portion oriented at a first angle relative to the outer support rim and an entry portion extending from the lead in portion and oriented at a second angle relative to the outer support rim, the first angle being different than the second angle, wherein terminal ends of the first and second leaflets define a slit therebetween; and
   a reinforcing rib on each of the first and second leaflets, each reinforcing rib extending from the outer support rim to the slit.

2. The surgical access port as recited in claim 1, wherein the second angle is greater than the first angle.

3. The surgical access port as recited in claim 1, wherein the reinforcing ribs traverse both the lead in portions and entry portions of the first and second leaflets.

4. The surgical access port as recited in claim 3, wherein the reinforcing ribs are centrally located on the first and second leaflets.

5. The surgical access port as recited in claim 2, further comprising an instrument seal positioned within the housing proximal to the duckbill valve.

6. The surgical access port as recited in claim 2, further comprising an end piece on a proximal end of the housing and having an opening for receipt of a surgical instrument.

7. The surgical access port as recited in claim 2, wherein the duckbill valve is formed of a synthetic rubber material.

8. The surgical access port as recited in claim 7, wherein the duckbill valve is formed of a polyisoprene.

9. The surgical access port as recited in claim 8, wherein the polyisoprene has a durometer of shore 30-40.

10. The surgical access port as recited in claim 2, further comprising a removable reducer cap positioned on the housing.

11. The surgical access port as recited in claim 2, wherein the elongate tubular member includes an enlarged indicia ring to limit the depth of penetration of the elongate tubular member.

12. A surgical access port assembly comprising:
    a cannula including a hollow housing having a hollow elongate tubular member extending from the housing and a duckbill valve positioned within the housing and having an outer support rim and first and second opposed leaflets extending inwardly of the outer support rim, each leaflet including a lead in portion oriented at a first angle relative to the outer support rim and an entry portion extending from the lead in portion and oriented at a second angle relative to the outer support rim, wherein terminal ends of the first and second opposed leaflets define a slit therebetween;

a reinforcing rib disposed on each of the first and second leaflets, each reinforcing rib extending from the outer support rim to the slit; and an obturator insertable through the cannula and having an elongate member terminating in a smooth obturator tip.

13. The surgical access port assembly as recited in claim 12, wherein the smooth obturator tip has a rounded distal tip.

14. The surgical access port assembly as recited in claim 12, wherein the smooth obturator tip has a conical distal tip.

15. A surgical access port comprising:

a hollow housing;

a hollow elongate tubular member extending from the housing, the elongate tubular member including a rigid proximal portion, a flexible central portion and a rigid distal portion;

a duckbill valve positioned within the housing and having an outer support rim and first and second opposed leaflets extending inwardly of the outer support rim, each leaflet including a lead in portion oriented at a first angle relative to the outer support rim and an entry portion extending from the lead in portion and oriented at a second angle relative to the outer support rim, wherein terminal ends of the first and second opposed leaflets define a slit therebetween; and a reinforcing rib disposed on each of the first and second opposed leaflets, each reinforcing rib extending from the outer support rim, across each respective entry portion and lead in portion to the slit.

16. The surgical access port as recited in claim 15, wherein the flexible portion is corrugated and includes a plurality of ribs.

17. The surgical access port as recited in claim 16, wherein the flexible portion is bendable so as to orient the rigid distal portion up to 180° relative to the rigid proximal portion.

18. The surgical access port as recited in claim 17, wherein the flexible portion is longitudinally extendable.

* * * * *